United States Patent [19]

Sakano et al.

[11] Patent Number: 4,476,128
[45] Date of Patent: Oct. 9, 1984

[54] 2-SUBSTITUTED THIAZOLYL-PIPERAZINE COMPOUNDS, PROCESS FOR PREPARATION THEREOF AND UTILIZATIONS THEREOF

[75] Inventors: Isao Sakano, Kanagawa; Shiyoichiro Miyahara; Yoshitsugu Yamada, both of Fukuoka; Yutaka Okazaki; Hiroshi Tokuda, both of Chiba; Akira Awaya; Takuo Nakano, both of Kanagawa, all of Japan

[73] Assignee: Mitsuitoatsu Chemicals, Inc., Tokyo, Japan

[21] Appl. No.: 458,311

[22] Filed: Jan. 13, 1983

Related U.S. Application Data

[62] Division of Ser. No. 237,754, Feb. 24, 1981, abandoned.

[30] Foreign Application Priority Data

Mar. 1, 1980 [JP] Japan ............... 55-024648

[51] Int. Cl.³ ............... A61K 31/495; C07D 417/04
[52] U.S. Cl. ............... 424/250; 544/367
[58] Field of Search ............... 424/250

[56] References Cited

U.S. PATENT DOCUMENTS 2,519,715 11/1947 Stewart ............... 544/360
2,602,796 7/1952 Stewart ............... 544/369
2,666,055 10/1952 Conroy ............... 544/360

FOREIGN PATENT DOCUMENTS 533657 11/1956 Canada ............... 544/369
2070603 9/1981 United Kingdom ............... 544/367

Primary Examiner—Donald G. Daus
Assistant Examiner—S. A. Gibson
Attorney, Agent, or Firm—Browdy & Neimark

[57] ABSTRACT

The present invention relates to a piperazine compound represented by the following general formula (I):

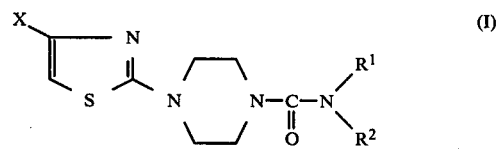

wherein X stands for a hydrogen atom or a phenyl group, $R^1$ stands for a hydrogen atom or an alkyl group, and $R^2$ stands for a hydrogen atom or an alkyl group.

These compounds are valuable as immunopotentiators, such as for the treatment of chronic rheumatoid arthritis and other diseases accompanied by reduction or abnormal change of the immune function.

2 Claims, No Drawings

2-SUBSTITUTED THIAZOLYL-PIPERAZINE COMPOUNDS, PROCESS FOR PREPARATION THEREOF AND UTILIZATIONS THEREOF

This is a division, of application Ser. No. 237,754 filed Feb. 24, 1981 now abandoned.

DETAILED DESCRIPTION OF THE INVENTION

The present invention relates to piperazine compounds, a process for the preparation thereof and a medicinal composition containing a piperazine compound as the active ingredient.

In accordance with the present invention, there is provided a novel piperazine compound represented by the following general formula (I):

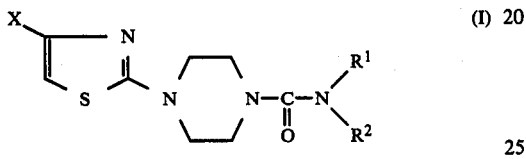

wherein X stands for a hydrogen atom or a phenyl group, $R^1$ stands for a hydrogen atom or an alkyl group, and $R^2$ stands for a hydrogen atom or an alkyl group.

In accordance with the present invention, there also is provided a process for the preparation of novel piperazine compounds represented by the following general formula (I):

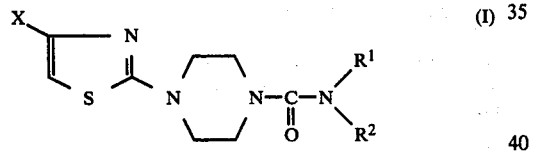

wherein X stands for a hydrogen atom or a phenyl group, $R^1$ stands for a hydrogen atom or an alkyl group, and $R^2$ stands for a hydrogen atom or an alkyl group, which comprises condensing a thiazole compound represented by the following general formula (II):

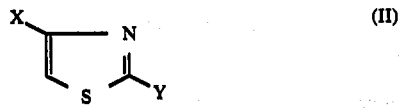

wherein X is as defined above and Y stands for a chlorine or bromine atom, with a piperazine compound represented by the following general formula (III):

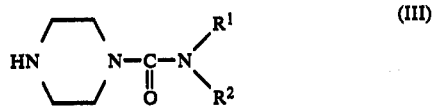

wherein $R^1$ and $R^2$ are as defined above.

Moreover, in accordance with the present invention, there is provided an immunopotentiator which comprises as the active ingredient a novel piperazine compound represented by the following general formula (I):

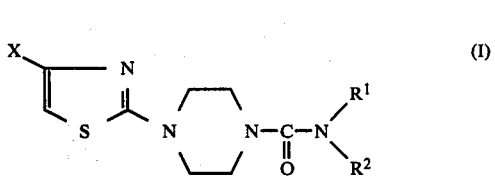

wherein X stands for a hydrogen atom or a phenyl group, $R^1$ stands for a hydrogen atom or an alkyl group, and $R^2$ stands for a hydrogen atom or an alkyl group.

This immunopotentiator is used for the treatment of chronic rheumatoid arthritis and other diseases accompanied by reduction of abnormal change of the immune function.

The novel piperazine compound is obtained by the reaction represented by the following reaction formula:

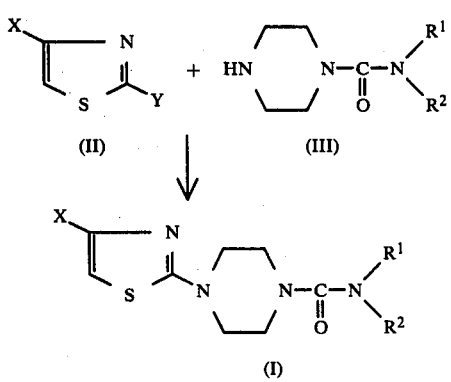

More specifically, the novel piperazine compound of the present invention is obtained by condensing a thiazole compound represented by the above general formula (II) in which X is as defined above with respect to the general formula (I) and Y is a chlorine or bromine atom, with a piperazine compound of the above general formula (III) in which $R^1$ and $R^2$ are as defined above with respect to the general formula (I), if desired, in a solvent inactive to the reaction, such as dioxane, tetrahydrofuran, dimethyl formamide, xylene, toluene, benzene, o-dichlorobenzene, methylene chloride or chloroform. The reaction is carried out at about 0° to about 200° C. and the reaction is substantially completed in 1 to 8 hours. More preferably, the reaction is carried out at 50° to 150° C., and the reaction is advantageously conducted at the boiling point of the solvent used. The reaction is ordinarily carried out in the presence of a base. As the base, there may be used organic and inorganic bases such as triethylamine, pyridine, sodium carbonate, sodium hydrogencarbonate and sodium hydride. Furthermore, the reaction proceeds advantageously with increased yield in the presence of copper catalyst.

The compound of the general formula (I), obtained by the above reaction, may be isolated and purified by usual procedures such as column chromatography, recrystallization and distillation under reduced pressure.

Furthermore, there may be adopted a method in which the product is purified in the form of an acid salt and it is then treated with an appropriate alkali to obtain a free base.

The compound of the general formula (II) or (III) may be prepared by known methods.

Specific examples of the novel piperazine compound prepared according to the present invention are as follows.

1-(4-Phenyl-2-thiazolyl)-SR4-carbamoylpiperazine, 1-(4-phenyl-2-thiazolyl)-4-methylcarbamoylpiperazine, 1-(4-phenyl-2-thiazolyl)-4-ethylcarbamoylpiperazine, 1-(4-phenyl-2-thiazolyl)-4-n-propylcarbamoylpiperazine, 1-(4-phenyl-2-thiazolyl)-4-i-propylcarbamoylpiperazine, 1-(4-phenyl-2-thiazolyl)-4-n-butylcarbamoylpiperazine, 1-(4-phenyl-2-thiazolyl)-4-i-butylcarbamoylpiperazine, 1-(4-phenyl-2-thiazolyl)-4-dimethylcarbamoylpiperazine, 1-(4-phenyl-2-thiazolyl)-4-diethylcarbamoylpiperazine, 1-(4-phenyl-2-thiazolyl)-4-di-i-propylcarbamoylpiperazine, 1-(4-phenyl-2-thiazolyl)-4-i-butylpropylcarbamoylpiperazine, N-methyl-N-ethyl-1-(4-phenyl-2-thiazolyl)-4-piperazinecarboxamide, N-methyl-N-i-propyl-1-(4-phenyl-2-thiazolyl)-4-piperazinecarboxamide, 1-(2-thiazolyl)-4-carbamoylpiperazine, 1-(2-thiazolyl)-4-methylcarbamoylpiperazine, 1-(2-thiazolyl)-4-ethylcarbamoylpiperazine, 1-(2-thiazolyl)-4-n-propylcarbamoylpiperazine, 1-(2-thiazolyl)-4-i-propylcarbamoylpiperazine, 1-(2-thiazolyl)-4-n-butylcarbamoylpiperazine, 1-(2-thiazolyl)-4-i-butylcarbamoylpiperazine, 1-(2-thiazolyl)-4-dimethyl carbamoylpiperazine, 1-(2-thiazolyl)-4-diethylcarbamoylpiperazine, 1-(2-thiazolyl)-4-di-i-propylcarbamoylpiperazine, 1-(2-thiazolyl)-4-i-butylpropyl-carbamoylpiperazine, N-methyl-N-ethyl-1-(2-thiazolyl)-4-piperazinecarboxamide and N-methyl-N-i-propyl-1(2-thiazolyl)-4-piperazinecarboxamide.

The compound of the present invention represented by the above general formula (I) has pharmacological activities. To our great surprise, it was found that the compound of the present invention has a high immunopotentiative action. The toxicity of the compound is very low. Accordingly, the compound of the present invention is very valuable as a medicine.

This point will now be described in detail with reference to the tests.

Various test systems using animals have been proposed for determining the immunopotentiative action. Results of the test of reinforcement of the delayed hypersensitivity, which is a typical test among these tests, will now be described.

The delayed hypersensitivity induced when picryl chloride (2-chloro-1,3,5-trinitrobenzene) is coated on the skin of a mouse is known as a typical cellular immunity, and this is one of test systems adopted broadly in the world [see Asherson, G. L. and Ptak, W: Contact and Delayed Hypersensitivity in the Mouse I, Active Sensitization and Passive Transfer, Immunology, 15, 405–416 (1968)].

This system was used for the test of reinforcement of the delayed hypersensitivity.

Test 1 (Test of Reinforcement of Delayed Hypersensitivity)

Test Procedures:

One group of eight ICR male mice, each having a body weight of about 30 g, was used for the test.

Sensitization was effected by coating a 7% solution of picryl chloride in a 4/1 mixture of olive oil and acetone on the shaved abdomen of the mouse.

Simultaneously with sensitization, a solution or suspension of the compound of the present invention in a 0.2% solution of carboxymethyl cellulose in a physiological saline was orally administered to the mouse at a dose of 50 mg per Kg of the body weight. To the control group, a 0.2% carboxymethyl cellulose solution in a physiological saline was similarly administered.

The delayed hypersensitivity was challenged 7 days after sensitization by gripping the ear of the mouse by a forceps wrapped with a felt impregnated with a 1% solution of picryl chloride in olive oil and coating the ear with the solution. The thickness of the ear was measured before challenging and 24 hours after challenging and the ratio of increase of the thickness (average value of both the ears in eight mice±standard deviation) was obtained as shown in Table 1.

For comparison, the test was similarly carried out by using Levamisole hydrochloride, and the obtained results are shown in Table 1. F.t tests were carried out. The group in which the test result was significant at a level of $P < 0.05$ was marked by *, and the group in which the test result was significant at a level of $P < 0.01$ was marked by **.

Results:

When the compound of the present invention was administered simultaneously with sensitization, the delayed hypersensitivity caused by challenging was reinforced, and the reinforcing effect was higher than that attained by Levamisole.

Thus, it was confirmed that the compound of the present invention has an actvity of activating the cellular immunity response (immunopotentiative action) in mice and this activity is higher than that of Levamisole.

TABLE 1

Results of Test of Reinforcement of Delayed Hypersensitivity

| Compound | Ratio of Increase of Ear Thickness (average value ± standard variation, %) |
|---|---|
| control | 28.1 ± 1.3 |

TABLE 1-continued

Results of Test of Reinforcement of Delayed Hypersensitivity

| Compound | Ratio of Increase of Ear Thickness (average value ± standard variation, %) |
|---|---|
| [4-phenyl-thiazol-2-yl piperazine N,N-diethylurea structure] | 37.5 ± 2.1** |
| [thiazol-2-yl piperazine N,N-diethylurea structure] | 36.6 ± 3.0* |
| Levamisole hydrochloride | 33.9 ± 3.0 |

The adjuvant arthritis in rats caused by injection of a Mycobacterium tuberculosis adjuvant is often utilized for a model test of chronic rheumatoid arthritis in men.

The mechanism of manifestation of this disease has not completely been elucidated, but it is known that the cellular immunity takes an important role. The immunopotentiative action of the compound of the present invention was tested according to this known adjuvant arthritis test.

Test 2 (Adjuvant Arthritis Test, Table 2)

Test Procedures:

A group of ten 9-weeks-old SD male rats were used for the test. In 0.1 ml of fluid paraffin, 0.4 mg of dry dead cells of Mycobacterium tuberculosis were suspended, and the suspension was injected under the heel skin of the right hind leg. The compound of the present invention was subcutaneously administered 9 times as a whole before and after injection of the adjuvant. The test compound was dissolved in a physiological saline and administered at a dose of 5 mg per Kg of the body weight. The swelling volume of the left hind leg as measured during the period of from the day of injection to the day of completion of the test, and the swelling ratio was calculated. For comparison, the test was similarly conducted by using Levamisole hydrochloride. The obtained results are shown in Table 2. F.t tests were carried out on the obtained test results. The group in which the test result was significant at a level of $P<0.05$ was marked by *, and the group in which the test result was significant at a level of $P<0.01$ was marked by **.

Results:

The secondary inflammation of the adjuvant arthritis was remarkably controlled by the compound of the present invention, and the effect was statistically significant with respect to the control group to which no compound was administered. The effect by the compound of the present invention was higher than that of Levamisole used as the reference compound but there is no statistically significant difference between the two compounds. Thus, it was confirmed that the compound of the present invention has an immunomodulating activity and an anti-arthritic activity and these activities are higher than those of Levamisole.

TABLE 2

Results of Adjuvant Arthritis Test

| Compound | Swelling Ratio (average value ± standard variation, %) | | |
|---|---|---|---|
| | 15 days | 18 days | 21 days |
| control | 86.4 ± 11.9 | 93.0 ± 11.0 | 87.0 ± 12.4 |
| [4-phenyl-thiazol-2-yl piperazine N,N-diethylurea structure] | 43.5 ± 13.9* | 41.5 ± 12.6** | 52.9 ± 11.2 |
| [thiazol-2-yl piperazine N,N-diethylurea structure] | 60.9 ± 8.0 | 59.8 ± 7.8* | 50.5 ± 10.0* |

TABLE 2-continued

| | Results of Adjuvant Arthritis Test | | |
|---|---|---|---|
| | Swelling Ratio (average value ± standard variation, %) | | |
| Compound | 15 days | 18 days | 21 days |
| Levamisole.hydrochloride | 54.6 ± 11.3 | 61.7 ± 9.8* | 73.3 ± 14.6 |

As illustrated in Tests 1 and 2, the compound of the present invention is very effective as the immunopotentiator, and therefore, the compound of the present invention is effective for remedy of diseases accompanied by reduction or abnormal change of the immune functions, for example, auto-immune diseases such as chronic rheumatoid arthritis.

As an immunotherapy of cancers, there can be considered a method in which a specific or non-specific immune function reduced by the cancer-bearing state is increased by some reaction or other and the resistance to cancer is given to the living body for remedy of cancer. Participation of macrophage in such reaction is indispensable. More specifically, (1) the activated macrophage has a cancer cellmediating cytotoxicity, (2) the macrophage is one of influential effector cells for the antibody-dependent cellmediating cytotoxicity, and (3) when a specific immunity to cancer cells is established and killer T cells are induced, the cancer antigen on the cancer cells should be transferred to the T cells and recognized as the antigen. For this purpose, the cancer cells mediated by the reactions (1) and (2) are phagocytized by the macrophage. Accordingly, the macrophage is very important for immunotherapy of cancers.

The results of the test of the action of the effective ingredient of the present invention on the macrophage will now be described with reference to the following Test 3. More specifically, the separated macrophage and EL-4 leukemic cell were mixed and cultured, and $^3$H-thymidine was added to a culture medium and the quantity of $^3$H-thymidine incorporated into the EL-4 cell was determined to examine the activity of the macrophage. When the macrophage is activated by administration of the effective ingredient of the present invention, inhibition of the growth of EL-4 cell, that is, phagocytosis of the cancer cell by the macrophage, is observed. Accordingly, if the take-in amount of $^3$H-thymidine is measured and this amount is reduced, it is confirmed that the macrophage has been activated.

Test 3 (In-Vitro Test of Inhibition of Growth of Cancer Cell by Macrophage)

Test Procedures:

To a group of three ddY female mice (having a body weight of 25 g), 0.5 ml of a suspension of 2 mg of the effective ingredient of the present invention in 5 ml of a physiological saline was intraperitoneally administered. The dose was 8 mg per Kg of the body weight. To the control group, a physiological saline was similarly administered. After passage of 4 days, exuded abdominal cells were collected and deposited on a plastic Petri dish to collect macrophages.

Then, $1 \times 10^6$ of so obtained macrophages and $1 \times 10^5$ of EL-4 leukemic cells of C57 BL/6J mouse were mixed and cultured in an RPMI 1640 culture medium to which 10% of bovine embryo serum was added (at 37° C. in the presence of 5% of $CO_2$) for 24 hours. Then, 0.1 μCi of $^3$H-thymidine was added and culturing was further conducted for 16 hours. Cells were collected on a filter paper from the culture medium and the amount of $^3$H-thymidine incorporated in was determined by a liquid scintillation counter. The take-in ratio (%) was calculated according to the following formula:

Take-in ratio (%) =

$$\frac{\text{(count number in case of mixed culturing)} - \text{(count number in case of single culturing of macrophages)}}{\text{(count number of single culturing of EL-4 cells)}} \times 100\%$$

The average value (%) in one group of three mice was determined to obtain results shown in Table 3. For comparison, the test was similarly carried out by using Levamisole hydrochloride.

Results:

It was confirmed that the effective ingredient of the present invention prominently inhibits take-in of $^3$H-thymidine by EL-4 leukemic cells while Levamisole hydrochloride does not exhibit such action.

More specifically, it was confirmed that the effective ingredient of the present invention activates the macrophage to cause phagocytosis of certain cancer cells, whereas Levamisole hardly exhibits such action.

TABLE 3

| Compound | In-Vitro Test of Inhibition of Growth of Cancer Cell by Macrophage — Take-in Ratio (average value, %) |
|---|---|
| control | 79.6 |
| (phenyl-vinyl-thiazole-piperazine-carbonyl-N(C₂H₅)₂ structure) | 21.0 |
| (thiazole-piperazine-carbonyl-N(C₂H₅)₂ structure) | 25.8 |
| Levamisole hydrochloride | 53.3 |

The results of treatment of cancers of certain animals by the effective ingredient of the present invention will now be described with reference to the following Tests 4 and 5.

Test 4 (Test of Antitumor Effect to Sarcoma 180 by Oral Administration)

Test Procedures:

One group of 6 ICR female mice were intradermally inoculated with $2 \times 10^6$ of Sarcoma 180 cells, and during a period of 10 days after passage of 24 hours, a solution or suspension of the effective compound in a physiological saline was orally administered at a dose of 0.1 ml per 10 g of the body weight once a day. To the control group, a physiological saline was similarly administered. The dose of the compound was 100 mg per Kg of the body weight. The diameter D (mm) of the tumor was measured, and the average value and the number N of the living mice were determined to obtain results shown in Table 4.

Results:

The inoculated tumor cells were propagated and grew into solid tumors. However, if the effective ingredient of the present invention was orally administered repeatedly, the tumor was diminished in size or disappeared.

For comprison, the test was similarly carried out by using Levamisole hydrochloride, but no substantial antitumor action was observed.

TABLE 4

Test of Antitumor Effect to Sarcoma 180 by Oral Administration

| Compound | Item | 0 | 2 | 4 | 6 | 8 | 10 |
|---|---|---|---|---|---|---|---|
| control | D | — | 7.3 | 17.0 | 24.4 | 28.5 | 35.7 |
|  | N | 6 | 6 | 6 | 6 | 5 | 2 |
| (phenyl-thiazole-piperazine-urea-N(C$_2$H$_5$)$_2$ compound) | D | — | 5.6 | 3.5 | 4.6 | 0 | 0 |
|  | N | 6 | 6 | 6 | 6 | 6 | 6 |
| (thiazole-piperazine-urea-N(C$_2$H$_5$)$_2$ compound) | D | — | 8.6 | 7.5 | 6.7 | 7.7 | 0 |
|  | N | 6 | 6 | 6 | 6 | 6 | 6 |
| Levamisole.hydrochloride | D | — | 8.1 | 16.8 | 23.1 | 27.4 | 25.5 |
|  | N | 6 | 6 | 6 | 6 | 6 | 5 |

Note
D: average diameter (mm) of tumor
N: number of living mice

Test 5 (Test of Antitumor Effect to Sarcoma 180 by Subcutaneous Administration)

Test Procedures:

The test was carried out in the same manner as described in Test 4 except that the effective compound was subcutaneously administered and the dose was changed to 20 mg per Kg of the body weight.

Results:

The change of the diameter D (mm) of the tumor was examined and the number of living mice was checked to obtain results shown in Table 5. Even if the dose was 1/5 of the dose adopted in case of oral administration, the same effect as obtained by oral administration could be obtained. In contrast, Levamisole hydrochloride had no substantial antitumor activity.

TABLE 5

Test of Antitumor Effect to Sarcoma 180 by Subcutaneous Administration

| Compound | Item | 0 | 2 | 4 | 6 | 8 | 10 |
|---|---|---|---|---|---|---|---|
| control | D | — | 9.3 | 15.6 | 21.1 | 29.7 | 38.4 |
|  | N | 6 | 6 | 6 | 5 | 3 | 2 |
| (phenyl-thiazole-piperazine-urea-N(C$_2$H$_5$)$_2$ compound) | D | — | 2.6 | 3.5 | 6.5 | 0.6 | 0 |
|  | N | 6 | 6 | 6 | 6 | 6 | 6 |
| (thiazole-piperazine-urea-N(C$_2$H$_5$)$_2$ compound) | D | — | 4.9 | 6.7 | 9.6 | 5.6 | 0 |
|  | N | 6 | 6 | 6 | 6 | 6 | 6 |
| Levamisole.hydrochloride | D | — | 3.6 | 14.1 | 22.2 | 26.8 | 23.8 |

TABLE 5-continued

| Test of Antitumor Effect to Sarcoma 180 by Subcutaneous Administration | | | | | | | |
|---|---|---|---|---|---|---|---|
| | | Lapse of Time (weeks) | | | | | |
| Compound | Item | 0 | 2 | 4 | 6 | 8 | 10 |
| | N | 6 | 6 | 6 | 6 | 3 | 2 |

Note
D: average diameter (mm) of tumor
N: number of living mice

The toxicity of the effective compound of the present invention will now be described with reference to the following Test 6.

Test 6 (Test of Acute Toxicity by Oral Administration)

Test Procedures:

A solution or suspension of the compound in a physiological saline was orally administered to one group of three ddY male mice, and after 7 days, the estimated LD$_{50}$ value was determined.

Results:

The estimated LD$_{50}$ value of the effective ingredient according to the present invention was in the range of from 600 to 1500 mg/Kg, which is much larger than the estimated LD$_{50}$ value of Levamisole hydrochloride, which was in the range of from 150 to 200 mg/Kg. Accordingly, it was confirmed that the toxicity of the compound of the present invention is very low.

When the compound of the present invention is used as a medicine, it may be used in the form of a free base. However, in view of the stability and easiness in formulation of a medicine, it is preferred that the compound be used in the form of a pharmaceutically acceptable salt such as a hydrochloride, a citrate or a phosphate, especially when a water solubility is required as in case of an injection.

The compound of the present invention can be administered in the form of a usual formulation according to a usual method adopted for conventional immunopotentiator agents. For example, as the preparation for oral administration, there can be mentioned a capsule, a granule, a pill, a fine granule, a tablet and a syrup. Furthermore, a suppository is suitable for direct administration of the rectum. Moreover, an injection for intravenous administration, subcutaneous administration or intramuscular administration may be used.

The immunopotentiator of the present invention may be used for remedy of diseases accompanied by reduction or abnormal change of the immunizing function, for example, auto-immune diseases such as chronic rheumatoid arthritis and multiple myositis, and various infectious diseases. Recovery of normalization of the immunizing function of patients suffering from these diseases can be rexpected by administration of the compound of the present invention. Mitigation of subjective symptoms and objective symptoms can be expected by administration of the compound of the present invention.

The administration method and preparation form may appropriately be chosen according to the kind of the disease and the condition of the patient. In case of oral administration, the dose of the compound of the present invention is 1 to 100 mg, preferably 1 to 20 mg, per Kg of the body weight per day. In case of administration to the rectum, the dose is preferably 1 to 100 mg per Kg of the body weight per day, in case of intravenous administration, the dose is preferably 1 to 10 mg per Kg of the body weight per day, and in case of subcutaneous or intramuscular administration, the dose is preferably 1 to 30 mg per Kg of the body weight per day.

It is preferred that the dose be appropriately adjusted according to the kind of the disease and the condition of the patient. The effect of the active compound of the present invention can be increased by using other medicines in combination appropriately according to the kind of the disease and the condition of the patient.

Medicines of the compound of the present invention can be prepared according to the customary formulas and methods adopted for ordinary immunopotentiator agents.

The present invention will now be described in detail with reference to the following Examples.

Example 1

[1-(4-phenyl-2-thiazolyl)-4-diethylcarbamoylpiperazine]

In 25 ml of dioxane were dissolved 1.85 g (0.01 mole) of 1-diethylcarbamoylpiperazine and 1.95 g (0.015 mole) of 2-chloro-4-phenylthiazole, and the mixture was heated and refluxed for 8 hours. The insoluble substance was removed and the filtrate was concentrated. The residue was washed with ether and subjected to silica gel chromatography to obtain 0.89 g (the yield being 25.8%) of crude 1-(4-phenyl-2-thiazolyl)-4-diethylcarbamoylpiperazine in the form of an oily product from a benzene-ether fraction. The crude product was recrystallized from an ether/hexane mixed solvent to obtain a purified product having a melting point of 76° to 77° C.

IR, $v_{max}^{KBr}$(cm$^{-1}$): 2980, 2940, 2860, 1650, 1525, 1490, 1450, 1430, 1385, 1345, 1250, 1225, 1190, 1165, 1120, 985, 925, 750

NMR (CDCl$_3$, 100 MHz) δ (ppm): 1.1 (6H, t, J=7.2 Hz), 3.0–3.7 (12H, m), 6.78 (1H, s), 7.1–8.0 (5H, m)

Elementary Analysis Values as C$_{18}$H$_{24}$N$_4$OS: Anal. Calcd for: C=62.76%, H=7.02%, N=16.27% S=9.31%; Found: C=62.95%, H=7.15%, N=16.31%, S=9.02%.

Example 2

[1-(4-phenyl-2-thiazolyl)-4-diethylcarbamoylpiperazine]

In 5 ml of dimethylformamide was dissolved 1.85 g (0.01 mole) of 1-diethylcarbamoylpiperazine, and 0.44 g (0.01 mole) of 55% sodium hydride was added to the solution with cooling by ice and the mixture was stirred for a time. Then, the mixture was stirred at room temperature for 1 hour. Then, the mixture was cooled again and a solution of 2.30 g (0.01 mole) of 2-bromo-4-phenylthiazole in 5 ml of dimethylformamide was gradually dropped to the mixture. Then, the mixture was heated at 70° C. for 8 hours. The post treatment was carried out in the same manner as described in Example 1 to obtain 1.75 g (the yield being 50.8%) of crude 1-(4-phenyl-2-thiazolyl)-4-diethylcarbamoylpiperazine in the form of an oily product. The crude product was recrystallized from an ether/hexane mixed solvent to obtain a purified product having a melting point of 76° to 77° C. The IR and NMR spectrum analysis results were the same as those of the product obtained in Example 1.

Example 3

A mixture of 5.6 g of 1-diethylcarbamoylpiperazine, 5.9 g of 2-chloro-4-phenylthiazole, 5.1 g of triethylamine, 1.0 g of copper powder and 40 ml of xylene was heated and refluxed for 8 hours. After the reaction, the insoluble substance was removed by filtration, and the solvent was removed from filtrate by distillation under reduced pressure. In the same manner as described in Example 1, the residue was subjected to silica gel chromatography and then recrystallized to obtain 5.8 g of a purified product which had the same melting point and IR and NMR spectrum analysis results of the product obtained in Example 1.

Example 4
[1-(2-thiazolyl)-4-diethylcarbamoylpiperazine]

In a mixed solvent of 20 ml of dioxane and 1 ml of dimethylformamide were dissolved 4.51 g (0.0244 mole) of 1-diethylcarbamoylpiperazine, 4.0 g (0.0244 mole) of 2-bromothiazole and 3.7 g (0.0366 mole) of triethylamine, and the mixture was heated and refluxed for 7 hours. The post treatment was carried out in the same manner as described in Example 1 to obtain 2.7 g (the yield being 41.2%) of crude 1-(2-thiazolyl)-4-diethylcarbamoylpiperazine in the form of an oily product. The crude product was subjected to distillation under reduced pressure to obtain a purified product having a boiling point of 187° to 189° C. at 3 mm Hg.

NMR (CCl$_4$, 100 MHz), $\delta$ (ppm): 1.12 (6H, t, J=6.4 Hz), 3.0–3.7 (12H, m), 6.48 (1H, d, J=3.6 Hz), 7.06 (1H, d, J=3.6 Hz)

Elementary Analysis Values as $C_{12}H_{20}N_4OS$: Anal. Calcd. for: C=53.70%, H=7.51%, N=20.88%, S=11.95%; Found: C=53.62%, H=7.76%, N=20.72%, S=11.58%

Example 5 [tablets containing 1-(4-phenyl-2-thiazolyl)-4-diethylcarbamoylpiperazine as effective ingredient]

A mixture of 50 g of 1-(4-phenyl-2-thiazolyl)-4-diethylcarbamoylpiperazine, 38 g of lactose, 35 g of corn starch and 20 g of crystalline cellulose was sufficiently stirred, and the mixture was kneaded and granulated with a solution of 5 g of hydroxypropyl cellulose in 100 ml of water and dried at 50° C. for 4 hours. The granulated mixture was mixed with 2 g of magnesium stearate and formed into tablets, each having a weight of 150 mg, by a tableting machine.

Example 6 [capsules containing 1-(4-phenyl-2-thiazolyl)-4-diethylcarbamoylpiperazine as effective ingredient]

A mixture of 100 g of 1-(4-phenyl-2-thiazolyl)-4-diethylcarbamoylpiperazine, 94 g of lactose, 60 g of corn starch 40 g of crystalline cellulose and 6 g of magnesium stearate was sufficiently stirred and filled into hard capsules in an amount of 300 mg per capsule by using an encapsulating machine.

Example 7 [granules containing 1-(4-phenyl-2-thiazolyl)-4-diethylcarbamoylpiperazine as effective ingredient]

A mixture of 100 g of 1-(4-phenyl-2-thiazolyl)-4-diethylcarbamoylpiperazine, 152 g of lactose, 140 g of corn starch and 80 g of crystalline cellulose was sufficiently stirred, and the mixture was kneaded and granulated with a solution of 20 g of hydroxypropyl cellulose in 400 ml of water and dried at 50° C. for 4 hours. The granules were passed through a 12-mesh screen to effect classification, and the granules were mixed with 8 g of magnesium stearate and the mixture was sufficiently stirred to obtain granules.

Example 8 [suppository containing 1-(4-phenyl-2-thiazolyl)-4-diethylcarbamoylpiperazine as effective ingredient]

A mixture of 10 g of 1-(4-phenyl-2-thiazolyl)-4-diethylcarbamoylpiperazine and 90 g of Witepsol ®W-35 (Dynamill Novel Chemicals, West Germany) was heated and molten at 60° C., and the melt was cast into molds so that the weight of each suppository was 1.5 g of 3 g. The cast melt was cooled and solidified to obtain suppositories.

Example 9 [tablets containing 1-(2-thiazolyl)-4-diethylcarbamoylpiperazine as effective ingredient]

A mixture of 50 g of 1-(2-thiazolyl)-4-diethylcarbamoylpiperazine, 38 g of lactose, 35 g of corn starch and 20 g of crystalline cellulose was sufficiently stirred, and the mixture was kneaded and granulated with a solution of 5 g of hydroxypropyl cellulose in 100 ml of water and dried at 50° C. for 4 hours. The granulated mixture was mixed with 2 g of magnesium stearate and formed into tablets, each having a weight of 150 mg, by a tableting Machine.

Example 10 [capsules containing 1-(2-thiazolyl)-4-diethylcarbamoylpiperazine as effective ingredient]

A mixture of 100 g of 1-(2-thiazolyl)-4-diethylcarbamoylpiperazine, 94 g of lactose, 60 g of corn starch 40 g of crystalline cellulose and 6 g of magnesium stearate was sufficiently stirred and filled into hard capsules in an amount of 300 mg per capsule by using an encapsulating machine.

Example 11 [suppository containing 1-(2-thiazolyl)-4-diethylcarbamoylpiperazine as effective ingredient]

A mixture of 10 g of 1-(2-thiazolyl)-4-diethylcarbamoylpiperazine and 90 g of Witepsol ®W-35 (Dynamill Novel Chemicals, West Germany) was heated and molten at 50° C., and the melt was cast into molds so that the weight of each suppository was 1.5 g or 3 g. The cast melt was cooled and solidified to obtain suppositories.

What is claimed is:

1. An immunopotentiator comprising a pharmaceutically acceptable diluent or carrier, and, as an effective ingredient, a piperazine compound represented by the following formula (I):

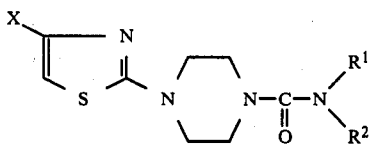

(I)

wherein X is a phenyl group, $R^1$ is a hydrogen atom or a $C_{1-4}$ alkyl group and $R^2$ is a hydrogen atom or a $C_{1-4}$ alkyl group, in the form of a free base or a physiologically acceptable acid salt.

2. A method for the treatment of chronic rheumatoid arthritis, a disease accompanied by reduction or abnormal change of the immune function, comprising administering to a patient having chronic rheumatoid arthritis an immunopotentiating amount of a compound of the general formula (I) or an inorganic or organic acid thereof:

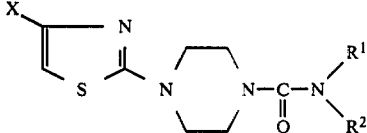

I)

wherein X is a hydrogen atom or is a phenyl group, $R^1$ is a hydrogen atom or a $C_{1-4}$ alkyl group and $R^2$ is a hydrogen atom or a $C_{1-4}$ alkyl group.

* * * * *